United States Patent
Yoon et al.

(10) Patent No.: US 10,952,674 B2
(45) Date of Patent: Mar. 23, 2021

(54) WIRELESS BATTERY-FREE DIAGNOSTIC MOUTH GUARD

(71) Applicant: University of Florida Research Foundation, Inc., Gainesville, FL (US)

(72) Inventors: Yong Kyu Yoon, Gainesville, FL (US); Xiaoyu Cheng, Mountain View, CA (US); Gloria Jung A. Kim, Evanston, IL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 623 days.

(21) Appl. No.: 15/573,548

(22) PCT Filed: May 13, 2016

(86) PCT No.: PCT/US2016/032353
§ 371 (c)(1),
(2) Date: Nov. 13, 2017

(87) PCT Pub. No.: WO2016/183442
PCT Pub. Date: Nov. 17, 2016

(65) Prior Publication Data
US 2018/0153469 A1    Jun. 7, 2018

Related U.S. Application Data

(60) Provisional application No. 62/160,713, filed on May 13, 2015.

(51) Int. Cl.
*A61B 5/00* (2006.01)
*A61B 5/22* (2006.01)
(Continued)

(52) U.S. Cl.
CPC ............ *A61B 5/682* (2013.01); *A61B 5/0004* (2013.01); *A61B 5/0015* (2013.01); *A61B 5/228* (2013.01);
(Continued)

(58) Field of Classification Search
CPC ....... A61B 5/682; A61B 5/228; A61B 5/0015; A61B 5/0004; A61B 5/4557;
(Continued)

(56) References Cited

U.S. PATENT DOCUMENTS 5,078,153 A    1/1992   Nordlander
6,089,864 A    7/2000   Buckner et al.
(Continued)

FOREIGN PATENT DOCUMENTS

CA    2698078 A1    9/2011
EP    1245197 A2    10/2002
(Continued)

OTHER PUBLICATIONS

International Search Report for PCT Application PCT/US2016/57908 dated Jan. 24, 2017.
(Continued)

*Primary Examiner* — Jacqueline Cheng
*Assistant Examiner* — Tho Q Tran
(74) *Attorney, Agent, or Firm* — Thomas|Horstemeyer, LLP

(57) ABSTRACT

Various examples of methods, systems, and apparatus are provided for monitoring using an improved mouth guard apparatus. In one example, a battery-free diagnostic mouth guard includes a biting force-voltage transducer comprising a piezoelectric film; a compact resonance tank comprising a wireless sensor; and a transmitting antenna for transmitting sensing data. A piezo-voltage from the biting force-voltage transducer can bias a varactor diode loaded on the wireless
(Continued)

sensor whose response frequency is tuned due to a capacitance change of the varactor diode. In some implementations, an external processing equipment can wirelessly detect a frequency shift of the varactor diode integrated resonator. In another example, a method includes detecting a biting force via a biting force-voltage transducer; biasing a varactor diode with a voltage from the transducer; tuning a response frequency of a split ring resonator using a capacitance change of the varactor diode; and emitting sensing data at the response frequency.

19 Claims, 5 Drawing Sheets

(51) Int. Cl.
  *H01Q 1/27* (2006.01)
  *A61C 19/04* (2006.01)
  *H01Q 9/16* (2006.01)
  *H02N 2/18* (2006.01)

(52) U.S. Cl.
  CPC .......... *A61B 5/4557* (2013.01); *H01Q 1/273* (2013.01); *H01Q 9/16* (2013.01); *A61B 2560/0214* (2013.01); *A61B 2562/0247* (2013.01); *A61C 19/04* (2013.01); *H02N 2/181* (2013.01)

(58) Field of Classification Search
  CPC .... A61B 2562/0247; A61B 2560/0214; H01Q 9/16; H01Q 1/273; H02N 2/181; A61C 19/04
  USPC ........................................ 600/587, 589, 590
  See application file for complete search history.

(56) References Cited

U.S. PATENT DOCUMENTS

| | | | |
|---|---|---|---|
| 6,122,961 | A | 9/2000 | Geen et al. |
| 6,638,241 | B2 | 10/2003 | Yerushalmy |
| 6,941,952 | B1 | 9/2005 | Rush, III |
| 8,217,784 | B2 | 7/2012 | Rastegar et al. |
| 8,466,794 | B2 | 6/2013 | Mack et al. |
| 8,537,017 | B2 | 9/2013 | Mack et al. |
| 8,554,495 | B2 | 10/2013 | Mack et al. |
| 9,526,289 | B2 | 12/2016 | MacK et al. |
| 9,554,607 | B2 | 1/2017 | Mack et al. |
| 2002/0094509 | A1 | 7/2002 | Durbin |
| 2004/0147237 | A1 | 7/2004 | Eckl et al. |
| 2004/0158194 | A1 | 8/2004 | Wolff et al. |
| 2005/0113654 | A1 | 5/2005 | Weber et al. |
| 2006/0064037 | A1* | 3/2006 | Shalon ................ A61B 5/1112 600/586 |
| 2006/0166157 | A1 | 7/2006 | Rahman |
| 2006/0210951 | A1 | 9/2006 | Levanoni et al. |
| 2006/0271199 | A1 | 11/2006 | Johnson |
| 2007/0106138 | A1 | 5/2007 | Beiski |
| 2007/0123949 | A1* | 5/2007 | Dabney ................ H03H 1/0007 607/37 |
| 2009/0210032 | A1 | 8/2009 | Beiski et al. |
| 2009/0220563 | A1 | 9/2009 | Shachar |
| 2009/0237236 | A1 | 9/2009 | Maassarani |
| 2009/0303076 | A1 | 12/2009 | Setiadi et al. |
| 2011/0008744 | A1 | 1/2011 | Teggatz |
| 2011/0066066 | A1 | 3/2011 | Van Kemenade et al. |
| 2011/0179851 | A1 | 7/2011 | Mack et al. |
| 2011/0184319 | A1 | 7/2011 | Mack et al. |
| 2011/0184663 | A1 | 7/2011 | Mack et al. |
| 2011/0205134 | A1* | 8/2011 | Blumberg, Jr. .... H01Q 15/0086 343/753 |
| 2012/0075692 | A1 | 3/2012 | Baik et al. |
| 2012/0123225 | A1 | 5/2012 | Al-Tawil |
| 2012/0172679 | A1 | 7/2012 | Logan |
| 2012/0236895 | A1 | 9/2012 | Miles |
| 2013/0066236 | A1 | 3/2013 | Herman et al. |
| 2013/0211270 | A1 | 8/2013 | St. Laurent et al. |
| 2014/0128932 | A1 | 5/2014 | Ewert et al. |
| 2014/0187875 | A1 | 7/2014 | Paris et al. |
| 2014/0188010 | A1 | 7/2014 | Paris et al. |
| 2014/0248574 | A1 | 9/2014 | Yoon et al. |
| 2014/0288574 | A1 | 9/2014 | Abramov |
| 2014/0312834 | A1 | 10/2014 | Tanabe et al. |
| 2015/0080768 | A1 | 3/2015 | Huang |
| 2015/0119759 | A1 | 4/2015 | Gonzales et al. |
| 2015/0305671 | A1 | 10/2015 | Yoon et al. |

FOREIGN PATENT DOCUMENTS

| | | |
|---|---|---|
| WO | 2005115225 A2 | 12/2005 |
| WO | 2008061328 A2 | 5/2008 |
| WO | 2010092171 A2 | 8/2010 |
| WO | 2014110548 A1 | 7/2014 |
| WO | 2016183442 A1 | 11/2016 |

OTHER PUBLICATIONS

International Search Report for PCT/US2014/011409 dated May 13, 2014.
Bluetooth Smart | Bluetooth Low Energy | BLE | Bluetooth | Bluetooth Technology Website at Bluetooth.com, Oct. 2015. http://www.bluetooth.com/Pages/Bluetooth-Smart.aspx., 2 pages.
The Wearables Report: Growth trends, consumer attitudes, and why smartwatches will dominate at Businessinsidercom, May 2015, http://www.businessinsider.com/the-wearable-computing-market-report-2014-10, 4 pages.
Yamada et al., "A stretchable carbon nanotube strain sensor for human-motion detection" by Nature Nanotechnology, vol. 6, pp. 296-301, Mar. 2011.
Huang et al.,"Electronic-Mechanical Coupling in Graphene from in situ Nanoindentation Experiments and Multiscale Atomistic Simulations" Nano Letter, vol. 11, No. 3, pp. 1241-1246, Feb. 2011.
Amjadi, et al., "Highly Stretchable and Sensitive Strain Sensor Based on Silver Nanowire-Elastomer Nanocomposite", ACS Nano, vol. 8, No. 5, pp. 5154-5163, Apr. 2014.
Jules Kieser et al., "Measuring Intraoral Pressure: Adaptation of a Dental Appliance Allows Measurement During Function", Dysphagia, (2008) vol. 23, No. 3, pp. 237-243.
Takahashi et al., "Effect of changes in the breathing mode and body position on tongue pressure with respiratory related oscillations", American Journal of Orthodontics and Dentofacial Orthopedics, (1999), vol. 115, No. 3, pp. 239-246.
K. Ahlberg et al., "Bruxism and sleep efficiency measured at home with wireless devices", Journal of Oral Rehabilitation, (2008) vol. 35, pp. 567-571.
Kim et al."Development of wireless bruxism monitoring device based on pressure sensitive polymer composite", Sensors and Actuators A, (2010) vol. 163, pp. 486-492.
J. Clauss et al., "In-vivo monitoring of bruxism with an intelligent tooth splint—Reliability and validity", IFMBE Proceedings, (Sep. 2009), vol. 25, No. 11, pp. 108-111.
Alvarez et al., "Diagnosis of Bruxism Based on Polymeric Piezoelectric Sensors and Remote Communication", [Online]. Available: http://www.disam.upm.es/, 6 pages.
Andres Diaz Lantada, Handbook of Active Materials for Medical Devices: Advances and Applications, Pan Stanford Publishing, Singapore, 2012, pp. 199-207.
Takeuchi et al., "A piezoelectric film based intrasplint detection method for bruxism", The Journal of Prosthetic Dentistry, (2001), vol. 86, issue 2, pp. 195-202.
González et al., "A wearable passive force sensor powered by an active interrogator intended for intra-splint use for the detection and recording of bruxism," Pervasive Computing Technologies for Healthcare, PervasiveHealth 2009, 3rd International Conference on, pp. 1-4.
Kim et al., "Development of Bite Guard for Wireless Monitoring of Bruxism Using Pressure-Sensitive Polymer," Body Sensor Networks (BSN), 2010 International Conference on Body Sensor Networks, pp. 109-116.

(56) References Cited

OTHER PUBLICATIONS

Raadsheer et al., "Contribution of Jaw Muscle Size and Craniofacial Morphology to Human Bite Force Magnitude", Journal of Dental Research, (Jan. 1999), vol. 78, No. 1, pp. 31-42.
No Author, mHealth New Horizons for Health Through Mobile Technologies, Global Observatory for eHealth Series, vol. 3, World Health Organization (Jun. 20, 2011), 112 pages.
Igarashi, Yoshimasa, "Analysis of the Denture Dynamics in RPD's'." 1989 Journal of Japanese Prosthdont Society, 33:369-375.
Agard et al., "Mouth guard for treating bruxism with electrostimulation," University of Wiconsin. Madison (Dec. 2001), pp. 1-27.
Humphries, Courtney, "Mouthpieces Gather Impact Data from Football Players", Mouthpieces Gather Impact Data from Football Players—MIT Technology Review (Oct. 2011), https://www.technologyreview.com/s/425724/mouthpieces-gather-impact-data-from-football-players/, pp. 1-5.
BiteStrip, up2dent, http://www.pxt.pt:8080/bitestripweb/FMPro?-DB=BS_SS_CMS.fp5&-Format=bs_insert.html&-Max=1&bsss=bs &sprache=au&seitenid=home&-Find, 1 page.
International Search Report for PCT/US2016/032353 dated Aug. 11, 2016.

\* cited by examiner

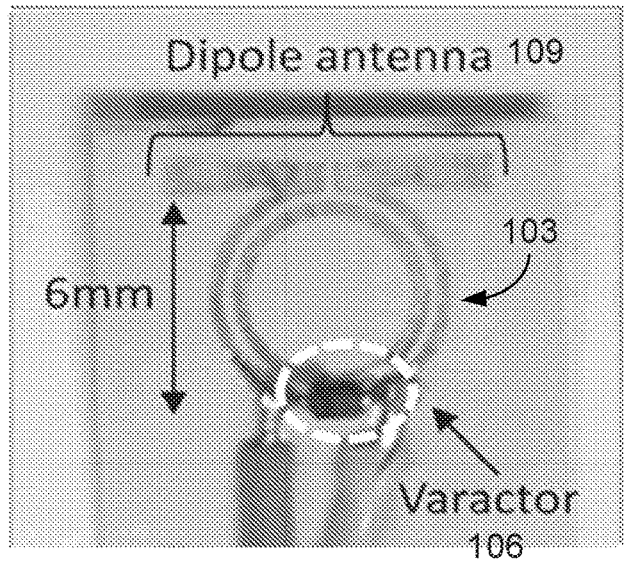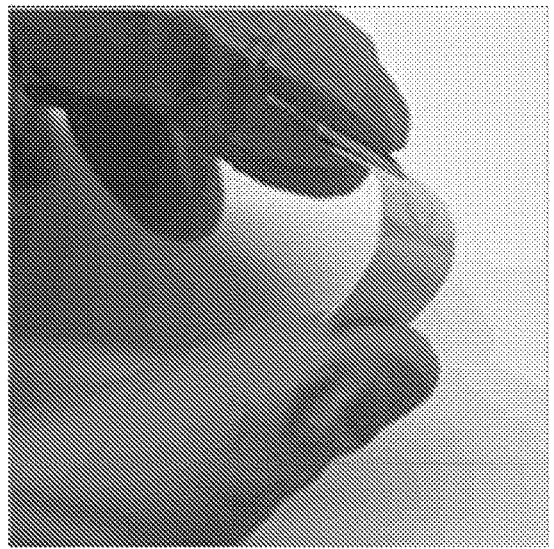
FIG. 4A          FIG. 4B
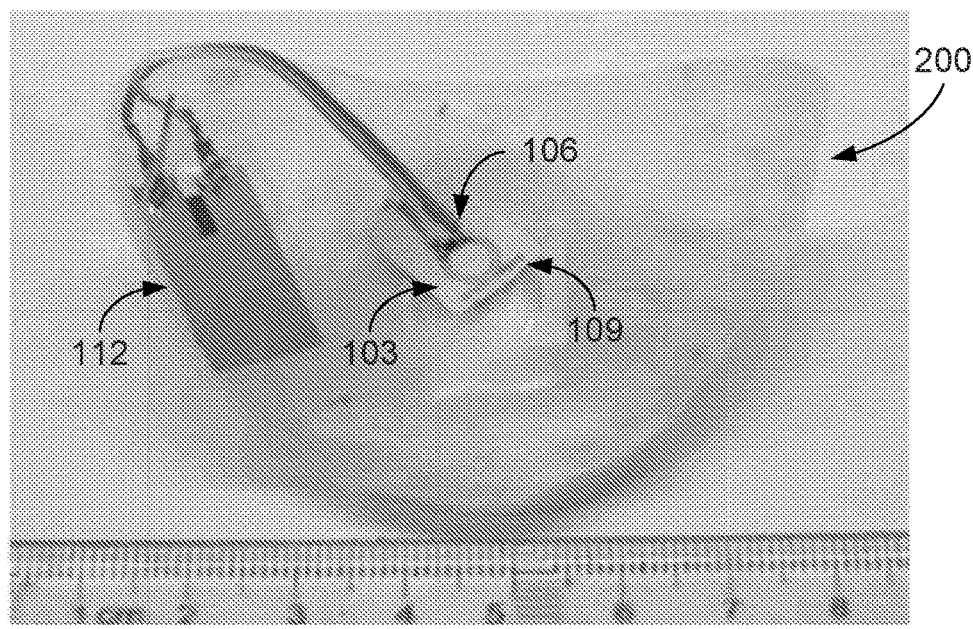
FIG. 5

WIRELESS BATTERY-FREE DIAGNOSTIC MOUTH GUARD

CROSS REFERENCE TO RELATED APPLICATIONS

This application is the 35 U.S.C. § 371 national stage application of PCT Application No. PCT/US2016/032353, filed May 13, 2016, which claims priority to, and the benefit of, U.S. provisional application entitled "WIRELESS BATTERY-FREE DIAGNOSTIC MOUTH GUARD" having Ser. No. 62/160,713, filed May 13, 2015, both of which are herein incorporated by reference in their entireties.

BACKGROUND

Bruxism involves the activities of grinding or clenching the teeth without functional purposes. Bruxism is one of the main contributors to temporomandibular disorder (TMD) and associated with chronic jaw pain and headache. As the second most common musculoskeletal pain, TMD affects about 10% of the general United States population. Intraoral sensing is of great interest for dentistry pathologies. Biting force measurement can be used for bruxism detection and management.

SUMMARY

Embodiments of the present disclosure are related to a monitoring system using an improved mouth guard apparatus.

In one embodiment, among others, a battery-free diagnostic mouth guard comprises a biting force-voltage transducer comprising a piezoelectric film; a compact resonance tank comprising a wireless sensor; and a transmitting antenna for transmitting sensing data. A piezo-voltage from the biting force-voltage transducer biases a varactor diode loaded on the wireless sensor whose response frequency is tuned due to a capacitance change of the varactor diode. In one or more aspects of these embodiments, the wireless sensor can comprise a split ring resonator. The split ring resonator can comprise a metamaterial particle. The split ring resonator can comprise at least two concentric rings with a slit carved on each of concentric ring. The varactor diode can be connected across the slit of one of the at least two concentric rings. The piezoelectric film can be coated with a layer of Polydimethylsiloxane (PDMS). The transmitting antenna can comprise a dipole antenna, which can be coupled to the wireless sensor or split ring resonator. The compact resonance tank can comprise a flexible substrate.

In another embodiment, a system comprises a battery-free diagnostic mouth guard and external processing equipment configured to wirelessly detect a frequency shift of a response frequency induced by a capacitance change of a varactor diode. The mouth guard can comprise a biting force-voltage transducer comprising a piezoelectric film; a compact resonance tank comprising a wireless sensor; and a transmitting antenna for transmitting sensing data. A piezo-voltage from the biting force-voltage transducer biases the varactor diode loaded on the wireless sensor whose response frequency is tuned due to the capacitance change of the varactor diode. In one or more aspects of these embodiments, the external processing equipment can comprise a receiving antenna, and the external processing equipment can be configured to read out the sensing data received by the receiving antenna. The sensing data can be transmitted over a MHz medical implant communication service (MICS) band or an industry science medicine (ISM) band. The wireless sensor can be configured to resonate at a frequency corresponding to the MICS band or the ISM band. The wireless sensor can be configured to resonate in a 5.8 GHz band. The response frequency of the wireless sensor can exhibit a substantially linearly change in response to force applied to the biting force-voltage transducer.

In another embodiment, a method comprises positioning a mouth guard between teeth of a subject, the mouth guard comprising a varactor diode, a split ring resonator, and a biting force-voltage transducer on a mouth guard substrate; generating a voltage corresponding to a biting force on the mouth guard substrate via the biting force-voltage transducer; biasing a varactor diode loaded on the mouth guard substrate with the voltage from the biting force-voltage transducer; tuning a response frequency of the split ring resonator based on a capacitance change of the varactor diode induced by the biasing; and emitting sensing data at the response frequency. In one or more aspects of these embodiments, the biting force-voltage transducer can comprise a piezoelectric film. The voltage generated via the biting force-voltage transducer can exhibit a substantially linearly change above a force of 240 N. The response frequency can be in a 2.4 GHz band. The method can further comprise determining a frequency shift of the response frequency based upon the sensing data.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 4A and 4B are images of an example of a varactor loaded tunable SRR in accordance with various embodiments of the present disclosure.

FIG. 5 is an image of an example of an assembled wireless battery-free mouth guard including the varactor loaded tunable SRR of FIGS. 4A and 4B in accordance with various embodiments of the present disclosure.

DETAILED DESCRIPTION

Figure 1A:
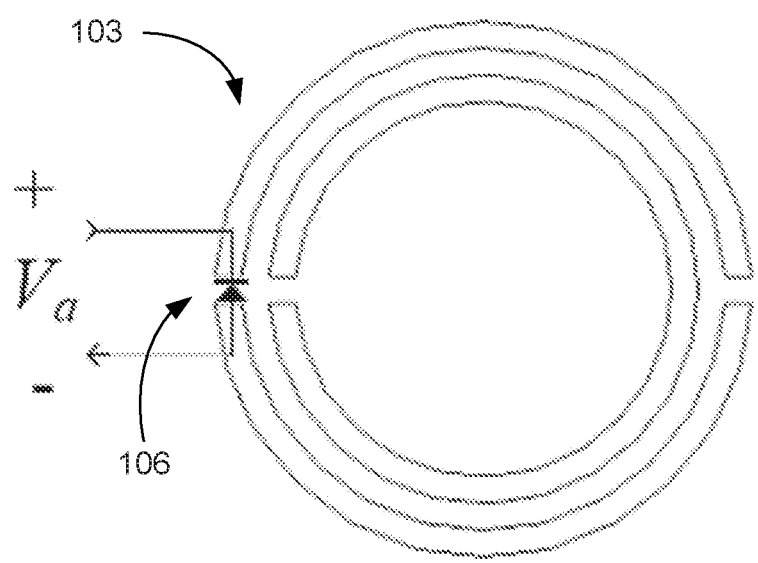
FIGS. 1A and 1B are a schematic representation and an equivalent circuit model for an example of a varactor loaded split ring resonator (SRR) in accordance with various embodiments of the present disclosure.

Disclosed herein are various embodiments of methods related to a monitoring system using an improved mouth guard apparatus. Reference will now be made in detail to the description of the embodiments as illustrated in the drawings, wherein like reference numbers indicate like parts throughout the several views.

Wired intraoral pressure sensing systems can be used for bruxism detection. However, the wired system restricts the patients' free movement. Also, due to the presence of a connection wire, the measurement is susceptible to noise and the measured data tends to be inaccurate. For example, a passive wireless bruxism sensor such as "BiteStrip" is available. However, the accuracy of this strip is limited by the electrode position, posture, and skin resistance. Active wireless bruxism sensors based on piezoelectric and force-resistance transducers may also be used. However, those systems are all based on microprocessors and wireless transceivers which are all energy hungry systems, and therefore monitoring and operation time is usually limited by battery capacity. Batteries are usually bulky and take up a major volume of the system. The usage of a battery for health and biomedical applications presents additional safety and packaging concerns. Also, the rigid circuitry loaded on the mouth guard may cause discomfort to the wearer.

In accordance with various embodiments of the present disclosure, a compact, wireless, and battery-free bruxism monitoring system can be designed, implemented, and characterized. In one embodiment, among others, a split ring resonator (SRR), a metamaterial particle as the compact resonance tank, is utilized. A piezoelectric film is employed as the biting force-voltage transducer.

In various implementations, after bruxism occurs, the piezo-voltage (which is proportional to the biting force) biases a varactor diode loaded on the SRR whose response frequency is then tuned due to the capacitance change of the varactor. Resonating the SRR causes the wireless signal to be transmitted via the coupled antenna. Frequency shift detection can be performed wirelessly using external processing equipment, such as external frequency sweeping equipment.

In one embodiment, due to the sub-wavelength nature of the SRR, the linear dimension of the resonator is, but not limited to, 0.31λ where λ is the wavelength of the resonant frequency, corresponding to a 38% size reduction compared to its half wavelength counterpart. Such a piezoelectric sensing system offers a battery-free solution for bruxism management. Since the whole system can be built on a flexible substrate, it can conform to different curvatures to adopt the mouth guard shape, ensuring comfort of the wearer. In one implementation, the pressure transducer showed a linear sensitivity of 306 KHz/N.

As discussed, an exemplary embodiment of the battery-free bruxism monitoring system utilizes a split ring resonator (SRR). The SRR comprises one of the metamaterial particles that offers negative permeability. The narrow bandwidth feature of the SRR makes it ideal for wireless sensing due to its high selectivity. The SRR is a sub-wavelength structure and can be used for device size reduction. The SRR can be tunable when it is loaded with a tunable component such as a varactor. All those attributes make the SRR suitable as a compact high performance wireless sensor.

In accordance with the present disclosure, an SRR-based, compact, wireless and battery-free sensor is integrated into a mouth guard for bruxism management. The integrated mouth guard reduces damage to the teeth, muscle, and jaw bone due to excessive grinding and clenching, and monitors the biting activities and behavior wirelessly without any battery being integrated. The sensing data outputted from the battery-free sensor can be read out by a receiving antenna and a frequency response measurement instrument outside the body.

A. Varactor Loaded Split Ring Resonator

In one embodiment, among others, an SRR 103 is composed of two concentric rings with a slit carved on each of them. Referring to FIG. 1A, shown is an example of the SRR 103. The outer ring has another (or second) slit, as shown in FIG. 1A, where a varactor 106 is loaded to achieve a tuning function.

Figure 1B:
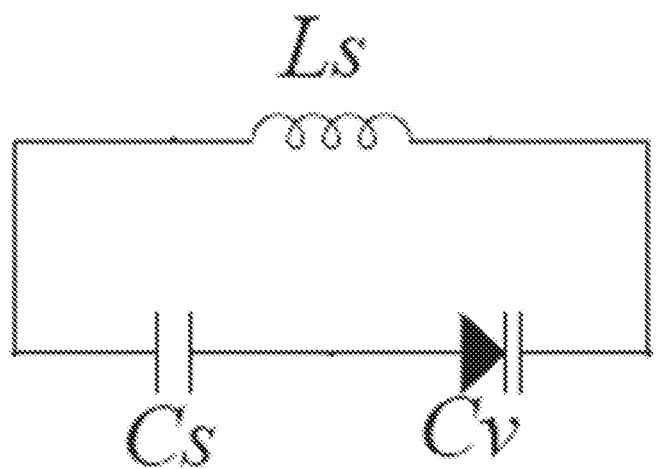

As shown in FIG. 1B, the SRR 103 with a varactor 106 can be modeled as an L-C tank with a tunable element $C_V$ which represents the varactor capacitance. $L_S$ and $C_S$ represent the inherent inductive and capacitive components of the SRR 103 and the resonance frequency of an SRR 103 can be determined by Eq. (1) below, where $C_{tot}$ represents the total effective capacitance.

$$f_s = \frac{1}{2\pi\sqrt{L_s C_{tot}}} \quad (1)$$

When reversely biased, the varactor diode demonstrates a tunable junction capacitance and it can be determined by:

$$C_V = \sqrt{\frac{q\varepsilon_s}{2(\Phi_i - V_a)} \frac{N_a N_d}{N_a + N_d}}, \quad (2)$$

where $N_a$ and $N_d$ are the doping densities of p-type and n-type semiconductors, respectively. $V_a$ is the negative biasing voltage, $\Phi_i$ is the built-in potential, and $\varepsilon_s$ is the permittivity of the semiconductor.

Eq. (2) indicates that the junction capacitance is reversely related to the square root of the biasing voltage. With varactor loading, the resonance frequency of the SRR can be modulated by the biasing voltage.

B. Piezoelectric Film and Varactor Diode

Piezoelectric represents the charges accumulated in materials due to mechanical stress or deformation of the material. In order to bias the varactor 106 (FIG. 1A), a piezoelectric sensor film (e.g., MEAS-DT, Measurement Specialties, Inc.) can be used. This is a piezo film for dynamic strain and vibration detection.

Figure 2:
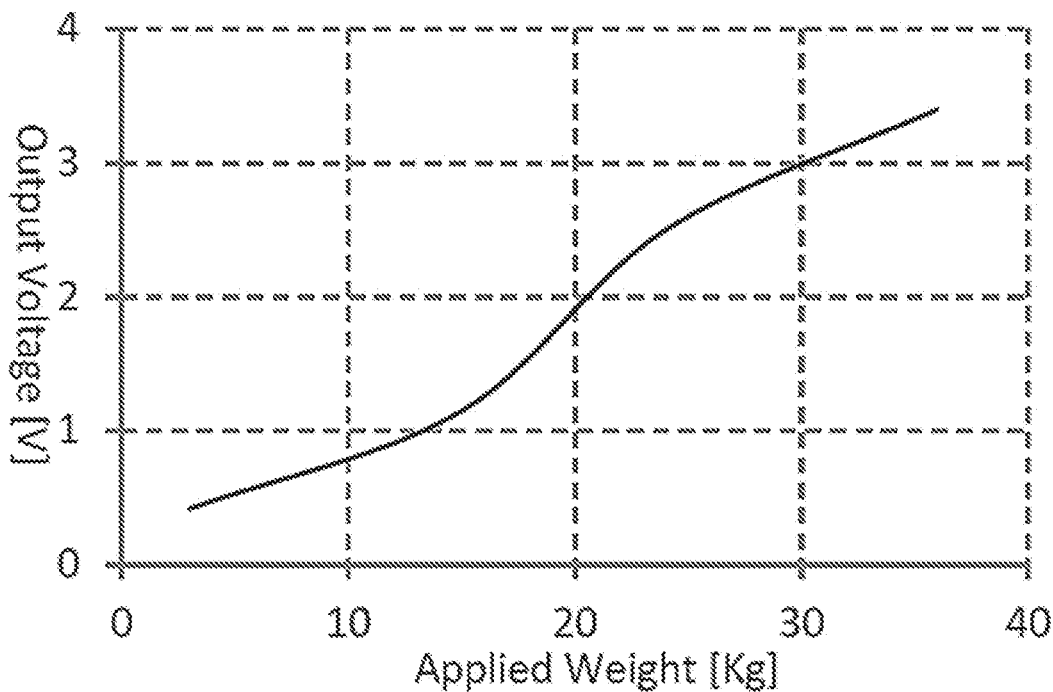
FIGS. 2 and 3 are plots illustrating examples of piezoelectric film characteristics and varactor tunability, respectively, in accordance with various embodiments of the present disclosure.

In accordance with an exemplary embodiment, the piezoelectric film can be characterized first. Standard weights can be used to mimic the human biting force. As different levels of weights are applied, the piezoelectric sensor output voltage level varies nearly linearly as shown in FIG. 2. It should be noted that the piezoelectric film has been coated with a layer of polydimethylsiloxane (PDMS) with a thickness of about 2 mm before characterization in the present embodiment. PDMS is an elastic and biocompatible material and makes the sensor less sensitive to ambient noise. It also prevents the sensor from direct contact with the intraoral biochemical media.

Figure 3:
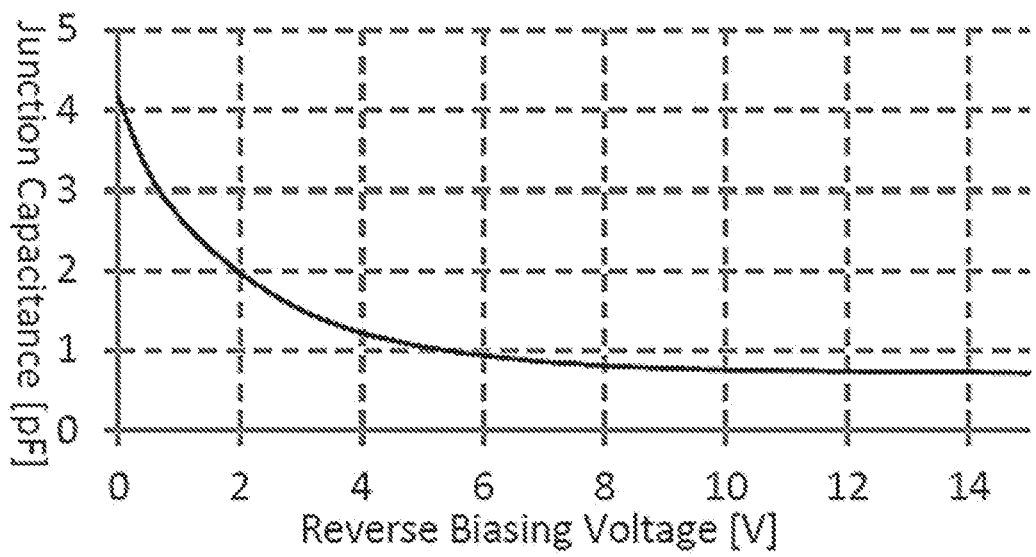

In one embodiment, the varactor 106 (e.g., SMV1232, Skyworks Inc.) can be a kind of hyper-abrupt junction tuning varactor with low resistance and is ideal for high Q resonator tuning. As shown in the example of FIG. 2, the piezoelectric film can exhibit a nearly linear output voltage up to 36 Kg applied weight, where 3.4V DC output voltage is observed across the output terminal of the film. From the varactor tunability example of FIG. 3, it can be seen that the varactor 106 demonstrates a large capacitance variation up to a reverse biasing voltage of 3.4V, which contributes to good sensitivity in the operating force range.

C. Sensor Fabrication and Characterization

In an exemplary embodiment, the SRR 103 loaded with a varactor 106 can be integrated with a dipole antenna 109 as shown in the image of FIG. 4A. The dipole antenna 109 can be used to enhance the coupling between the sensor and the external applicator antenna (not shown). In one embodiment, the system is fabricated on a high frequency laminate (RO 3010, Rogers Inc.), which is based on ceramic-filled polytetrafluoroethylene (PTFE) with a dielectric constant of 10.2, a loss tangent of 0.002, and a thickness of 10 mil (0.25 mm). Due to the small thickness, the sensor system is flexible and can be bent to fit a mouth guard curvature as shown in FIG. 4B.

In an exemplary embodiment, the SRR 103 is designed to, but not limited to, resonate at a 5.8 GHz band, with an outer diameter of 6 mm (0.31λ), and a trace width of 0.3 mm. An example of the whole mouth guard 200 with a battery-free bruxism detection system comprising of a piezoelectric film 112, a tunable SRR 103, and a dipole antenna 109 is assembled as shown in FIG. 5.

Figure 6A:
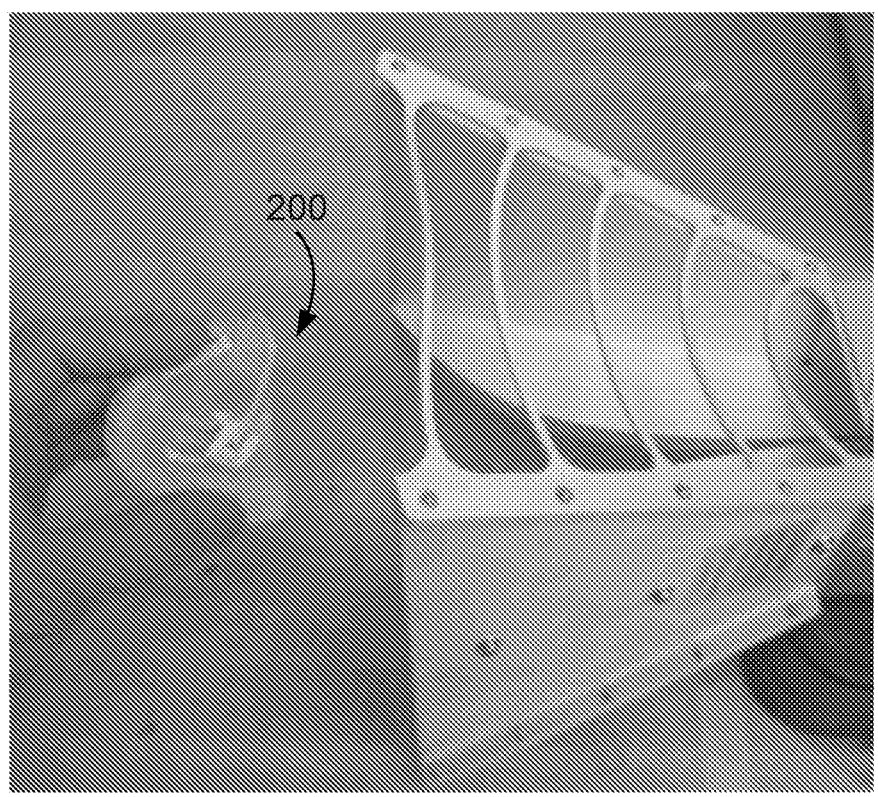
FIG. 6A is an image of an example of a measurement setup used for testing the wireless battery-free mouth guard of FIG. 5 in accordance with various embodiments of the present disclosure.

Measurements discussed below are performed using an Agilent E5071C vector network analyzer (VNA) for an example of the mouth guard 200. A broadband horn antenna was used as an applicator antenna, and S11 was measured. The applicator antenna was kept 30 mm away from the wireless mouth guard. Prior to measurements, the VNA was calibrated and an image of the measurement setup is shown in FIG. 6A.

Figure 6B:
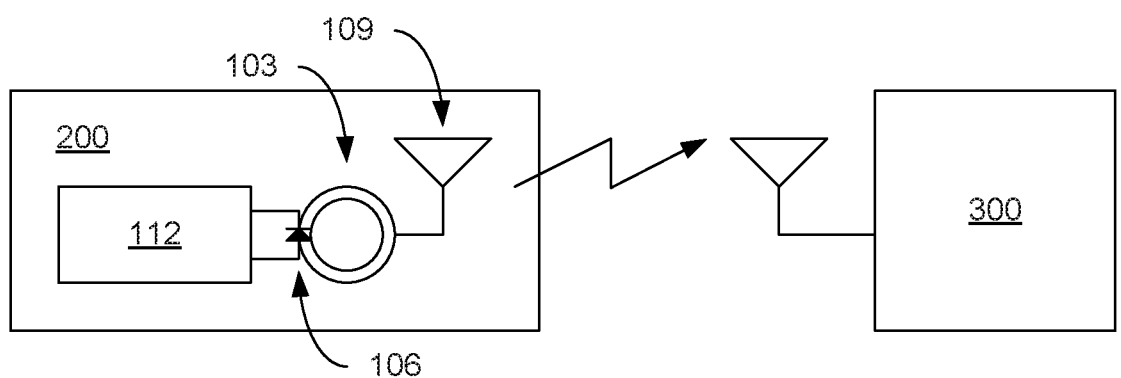
FIG. 6B is a schematic diagram illustrating an example of a system for monitoring the wireless battery-free mouth guard of FIG. 5 in accordance with various embodiments of the present disclosure.

Referring to FIG. 6B, shown is an example of a system including a mouth guard 200 in communication with external processing equipment 300 configured to analyze the transmitted signals. The diagnostic mouth guard 200 is battery-free and includes a biting force-voltage transducer comprising a piezoelectric film 112. The mouth guard 200 also includes a compact resonance tank comprising a wireless sensor including a SRR 103, which is coupled to a transmitting antenna 109 (e.g., a dipole antenna) for transmitting sensing data to the external processing equipment 300. A piezo-voltage generated by the biting force-voltage transducer is applied to a varactor diode 106 loaded on the wireless sensor (e.g., SRR 103). Biasing the varactor diode 106 changes its capacitance, which tunes the response frequency of the wireless sensor. The wireless sensor can be a SRR 103, and the SRR 103 can include a metamaterial particle. The SRR 103 can comprise two or more concentric rings with a slit carved on each of the rings. The varactor diode 106 is connected across a slit of one of the concentric rings (e.g., the outer ring). The piezoelectric film 112 can be coated with a layer of Polydimethylsiloxane (PDMS). The compact resonance tank comprises a flexible substrate.

The external processing equipment 300 comprises processing circuitry configured to wirelessly detect a frequency shift of the response frequency induced by the capacitance change of the varactor diode 106. The external processing equipment 300 includes a receiving antenna. The external processing equipment can be configured to read out the sensing data received by the receiving antenna. The sensing data can be transmitted over a MHz medical implant communication service (MICS) band or an industry science medicine (ISM) band, or other appropriate frequency band (e.g., 2.4 GHz). The wireless sensor can be configured to resonate at a frequency corresponding to the MICS band or the ISM band (e.g., a 5.8 GHz band), or other appropriate frequency band. As discussed, the response frequency of the wireless sensor exhibits a substantially linearly change in response to force applied to the biting force-voltage transducer.

By positioning the mouth guard 200 between the teeth of a subject, a voltage corresponding to a biting force on the mouth guard substrate can be generated via the biting force-voltage transducer (e.g., piezoelectric film 112). The voltage generated via the biting force-voltage transducer can exhibit a substantially linearly change above a force of 240 N. The voltage can be applied to the varactor diode 106 loaded on the mouth guard substrate to bias the varactor diode 106 and tune a response frequency of the SRR 103 based on a capacitance change of the varactor diode 106 induced by the biasing. Resonating the SRR 103 emits a signal or sensing data at the response frequency via the antenna 109. The external processing equipment 300 can monitor the emitted signal or sensing data through an antenna and determine a frequency shift of the response frequency based upon the signal or sensing data.

Figure 7:
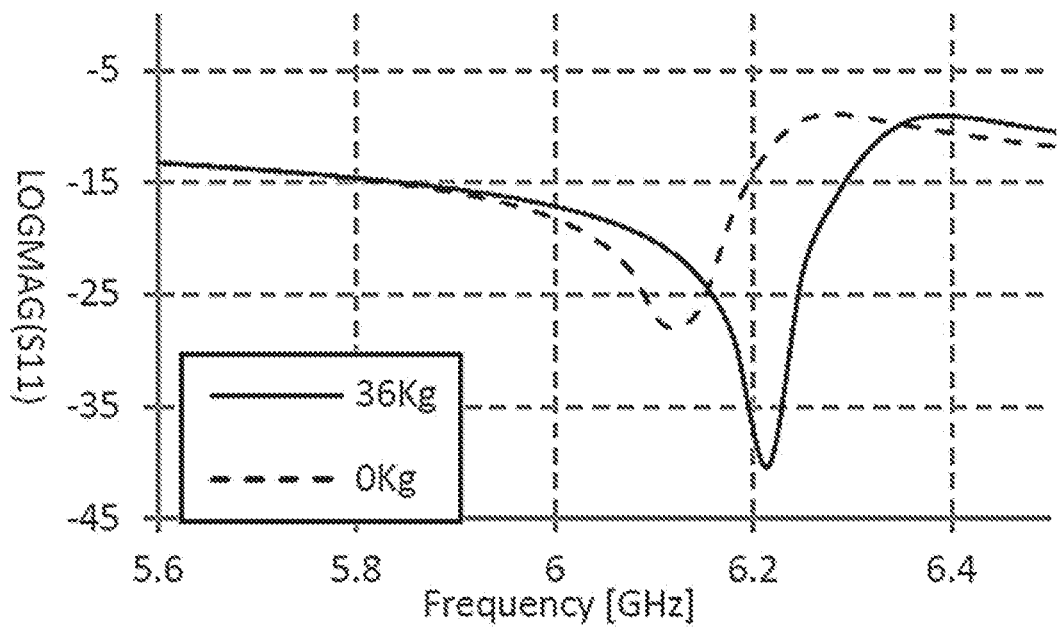
FIGS. 7 and 8 are plots illustrating examples of measured frequency response and resonance frequency shift, respectively, of the wireless battery-free mouth guard of FIG. 5 in accordance with various embodiments of the present disclosure.

FIG. 7 shows an example of the return loss spectra as a function of the different force input. The force applied on the piezoelectric film 112 (FIG. 5) modulates the output voltage of the film 112, which changes the equivalent capacitance of the varactor 106 (FIG. 5) according to the examples illustrated in FIGS. 2 and 3, resulting in the resonance frequency shift of FIG. 7. The relationship between the weight applied on the piezoelectric sensor and the output is shown in FIG. 8.

Figure 8:
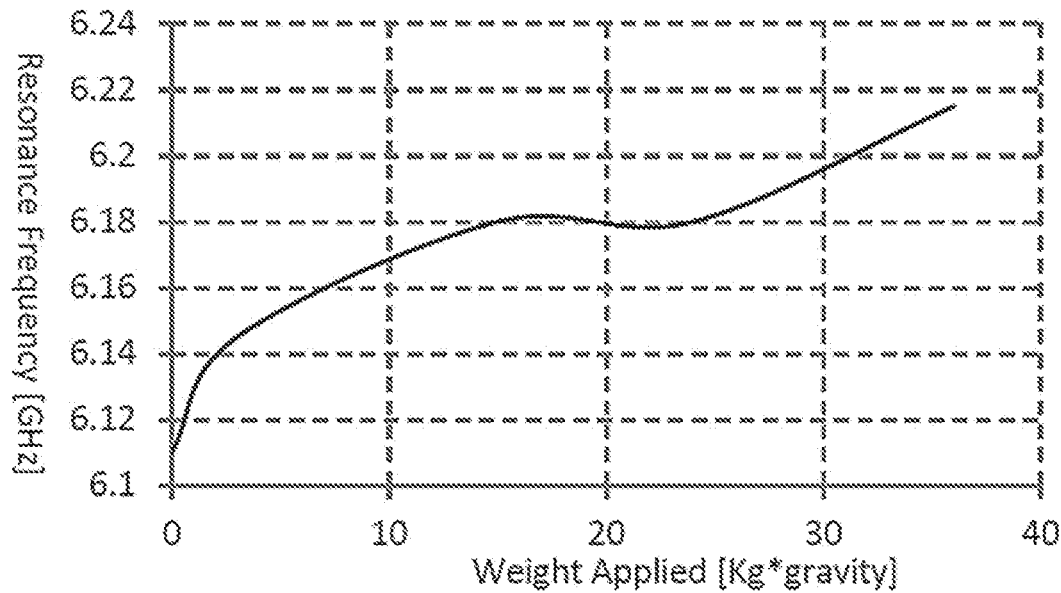

As demonstrated in FIG. 8, a nearly linear performance is obtained, although the SRR tunability is affected by its nonlinear behavior. The resonance frequency stays nearly constant after a certain capacitance value. This phenomenon may affect small force detection. As bruxism usually deals with a large force in a range of about 25-35 Kg*9.8 m/s$^2$ (or about 245 N to about 343 N), the usage of this sensor is highly advantageous. The system shows a linear sensitivity of 306 KHz/N.

In accordance with the present disclosure, embodiments of a compact wireless and battery-free mouth guard system 200 (FIG. 5) for bruxism management are presented based on a flexible metamaterial particle integrated with a varactor, a piezoelectric transducer, and a dipole antenna. In an exemplary embodiment, a linear size reduction of up to 38% is achieved compared to a half wavelength resonator. Good linearity in a useful force range (e.g., above 240 N) is observed from the sensor, and this system offers a platform for wireless battery-free biomedical sensing for force and strain.

Various aspects of the present disclosure include embodiments of a method for providing the diagnostic mouth guard. An exemplary embodiment includes positioning a varactor diode, a split ring resonator, and a biting force-voltage transducer on a mouth guard substrate; detecting a biting force on the mouth guard substrate via the biting force-voltage transducer; biasing a varactor diode loaded on the mouth guard substrate with a voltage from the biting force-voltage transducer; tuning a response frequency of a split ring resonator based on a capacitance change of the varactor diode; and emitting sensing data at the response frequency.

Various aspects of the present disclosure include a system comprising the diagnostic mouth guard and the external processing equipment. In any one or more aspects of the system, the external processing equipment can be configured to obtain the pressure sensor data from processing circuitry of the diagnostic mouth guard. The external processing equipment can be configured to process the obtained sensor data to determine a condition of bruxism. The external processing equipment can be configured to initiate an intervention in response to the determination of the condition of bruxism. The intervention can be an initiation of feedback provided by the diagnostic mouth guard. The feedback provided by the diagnostic mouth guard can be a vibration. In any one or more aspects of the system, the external processing equipment can be configured to provide an indication of the condition of bruxism through a graphical user interface (GUI).

The external processing equipment 300 (FIG. 6B) includes an antenna and transceiver (or receiver) that receives the transmitted sensor information for analysis and processing by processing circuitry. A data signal from the diagnostic mouth guard is transmitted over a wireless channel (or link) through a transmitting antenna 109 (FIG. 6B) and received by receiving antenna and transceiver (or receiver) at the external processing equipment 300. Transmission between the mouth guard 200 (FIG. 6B) and the external processing equipment 300 may be over, e.g., a 2.4 GHz communication link, a MHz medical implant communication service (MICS) band, or other industry science medicine (ISM) bands including, e.g., 433 MHz, 915 MHz, and 5.8 GHz.

In various embodiments, a battery-free diagnostic mouth guard 200 is disclosed that includes one or more pressure sensors and circuitry such as, e.g., a compact resonance tank in communication with the pressure sensors. The circuitry is configured to provide pressure sensor data to an external processing equipment when located in an oral cavity. The circuitry can include a compact resonance tank with, e.g., a varactor 106 (FIG. 6B) loaded on a SRR 103 (FIG. 6B) to achieve a tuning function, and an antenna 109 (FIG. 6B) embedded in the mouth guard 200. The circuitry can be configured to communicate with the external processing equipment 300 over a wireless channel.

The external processing equipment 300 can comprise a computing device (e.g., desktop computer, laptop, tablet, smartphone, personal digital assistant, or other system with like capability) or other analysis equipment (e.g., frequency analyzer, vector network analyzer, or other analysis system with like capability) suitable for detecting a frequency shift in the emitted signal or sensing data that is received via an antenna. Embodiments of the present disclosure can be implemented in hardware (e.g., mechanical and electrical), software, firmware, or a combination thereof. The computing device or analysis equipment can include at least one processor circuit, for example, having a processor and a memory, both of which are coupled to a local interface. Coupled to, or integrated in, the computing device or analysis equipment are various interface devices such as, for example, a display, a keyboard, and/or a touchpad or mouse. Various components can be stored in the memory and executed by the processor to provide various functionality disclosed by the present invention. For instance, an operating system and a frequency analysis application can be stored in the memory for execution by the processor. The frequency analysis application can be executed by the processor in order to detect or identify a frequency shift caused by force being applied to the mouth guard 200 as described above.

In this respect, the term "executable" means a program file that is in a form that can ultimately be run by the processor. An executable program may be stored in any portion or component of the memory including, for example, random access memory, read-only memory, a hard drive, compact disk (CD), floppy disk, or other memory components. The memory is defined herein as both volatile and nonvolatile memory and data storage components. Also, where the frequency analysis application may comprise software or code, each can be embodied in any non-volatile computer-readable medium for use by or in connection with an instruction execution system such as, for example, a processor in a computer system or other system. In this sense, the logic may comprise, for example, statements including instructions and declarations that can be fetched from the computer-readable medium and executed by the instruction execution system. In the context of the present invention, a "computer-readable medium" can be any medium that can contain, store, or maintain the frequency analysis application for use by or in connection with the instruction execution system.

Although the frequency analysis application is described as being embodied in software or code executed by a processor circuit as discussed above, as an alternative the same may also be embodied in dedicated hardware or a combination of software/general purpose hardware and dedicated hardware. If embodied in dedicated hardware, the processor circuit application can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, programmable gate arrays (PGA), field programmable gate arrays (FPGA), or other components, etc. Such technologies are generally well known by those skilled in the art and, consequently, are not described in detail herein.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

The invention claimed is:

1. A battery-free diagnostic mouth guard configured for positioning between teeth of a user, the mouth guard comprising:
   a biting force-voltage transducer comprising a piezoelectric film;
   a split ring resonator coupled to the biting force-voltage transducer;
   a varactor diode configured to load the split ring resonator; and
      a transmitting antenna, coupled to the split ring resonator, for transmitting sensing data from the biting force-voltage transducer;
   wherein a piezo-voltage from the biting force-voltage transducer biases the varactor diode loaded on the split ring resonator so as to change capacitance of the varactor diode and to cause a shift in resonant frequency of the split ring resonator.

2. The battery-free diagnostic mouth guard of claim 1, wherein the split ring resonator comprises a metamaterial particle.

3. The battery-free diagnostic mouth guard of claim 1, wherein the split ring resonator comprises at least two concentric rings with a slit carved on each concentric ring.

4. The battery-free diagnostic mouth guard of claim 3, wherein the varactor diode is connected across the slit of one of the at least two concentric rings.

5. The battery-free diagnostic mouth guard of claim 1, wherein the piezoelectric film is coated with a layer of Polydimethylsiloxane (PDMS).

6. The battery-free diagnostic mouth guard of claim 1, wherein the transmitting antenna comprises a dipole antenna.

7. The battery-free diagnostic mouth guard of claim 6, wherein the dipole antenna is coupled to the split ring resonator.

8. The battery-free diagnostic mouth guard of claim 1, wherein the split ring resonator comprises a flexible substrate.

9. A system comprising:
   a battery-free diagnostic mouth guard configured for positioning between teeth of a user, the battery-free diagnostic mouth guard comprising:
      a biting force-voltage transducer comprising a piezoelectric film;
      a split ring resonator; and
      a transmitting antenna for transmitting sensing data from the biting force-voltage transducer,
      wherein a piezo-voltage from the biting force-voltage transducer biases a varactor diode loaded on the split ring resonator so as to change capacitance of the varactor diode and to cause a shift in resonant frequency of the split ring resonator; and
   external processing equipment configured to wirelessly detect a frequency shift of the resonant frequency induced by the capacitance change of the varactor diode.

10. The system of claim 9, wherein the external processing equipment comprises a receiving antenna, wherein the external processing equipment is configured to read out the sensing data received by the receiving antenna.

11. The system of claim 9, wherein the sensing data is transmitted over a MHz medical implant communication service (MICS) band or an industry science medicine (ISM) band.

12. The system of claim 11, wherein the wireless sensor is configured to resonate at a frequency corresponding to the MICS band or the ISM band.

13. The system of claim 12, wherein the wireless sensor is configured to resonate in a 5.8 GHz band.

14. The system of claim 9, wherein the resonant frequency of the split ring resonator exhibits a substantially linear frequency shift in response to force applied to the biting force-voltage transducer.

15. A method comprising:
   positioning a mouth guard between teeth of a subject, the mouth guard comprising a varactor diode, a split ring resonator, and a biting force-voltage transducer on a mouth guard substrate, the varactor diode configured to load the split ring resonator;
   generating, by the biting force-voltage transducer, a voltage corresponding to a biting force on the mouth guard substrate;
   biasing the varactor diode by applying the voltage from the biting force-voltage transducer across the varactor diode;
   tuning a resonant frequency of the split ring resonator based on a capacitance change of the varactor diode induced by the biasing; and
   emitting sensing data from the biting force-voltage transducer.

16. The method of claim 15, wherein the biting force-voltage transducer comprises a piezoelectric film.

17. The method of claim 16, wherein the voltage generated via the biting force-voltage transducer exhibits a substantially linear change above a force of 240 N.

18. The method of claim 15, further comprising determining a frequency shift of the resonant frequency based upon the sensing data.

19. The method of claim 18, wherein the resonant frequency is in a 2.4 GHz band.

* * * * *